(12) United States Patent
Epstein

(10) Patent No.: US 12,298,983 B1
(45) Date of Patent: May 13, 2025

(54) SYSTEM AND METHOD FOR DETERMINING ACTIVITIES OF A USER BASED ON LOCATION

(71) Applicant: Joseph Alan Epstein, Pleasanton, CA (US)

(72) Inventor: Joseph Alan Epstein, Pleasanton, CA (US)

( * ) Notice: Subject to any disclaimer, the term of this patent is extended or adjusted under 35 U.S.C. 154(b) by 0 days.

(21) Appl. No.: 16/046,032

(22) Filed: Jul. 26, 2018

Related U.S. Application Data

(60) Provisional application No. 62/543,374, filed on Aug. 10, 2017.

(51) Int. Cl.
| | |
|---|---|
| *G06F 16/2457* | (2019.01) |
| *A61B 5/00* | (2006.01) |
| *A61B 5/11* | (2006.01) |
| *G06F 16/9537* | (2019.01) |
| *G06N 5/04* | (2023.01) |
| *H04L 67/50* | (2022.01) |

(52) U.S. Cl.
CPC ...... *G06F 16/24575* (2019.01); *A61B 5/1112* (2013.01); *A61B 5/1118* (2013.01); *A61B 5/4866* (2013.01); *G06F 16/9537* (2019.01); *G06N 5/04* (2013.01); *H04L 67/535* (2022.05)

(58) Field of Classification Search
CPC ........... G06F 16/24575; G06F 19/3481; G06F 3/048; G06F 3/0482; A63B 24/0062
USPC ......................................................... 707/776
See application file for complete search history.

(56) References Cited

U.S. PATENT DOCUMENTS

| | | | |
|---|---|---|---|
| 8,615,377 B1 * | 12/2013 | Yuen ...................... | A61B 5/222 702/160 |
| 8,738,321 B2 * | 5/2014 | Yuen .................... | A61B 5/0022 702/160 |
| 9,449,084 B2 * | 9/2016 | Chong ................... | H04H 60/65 |
| 9,454,751 B1 | 9/2016 | Dickerson et al. | |
| 9,589,270 B2 * | 3/2017 | Weiss ..................... | G06Q 30/02 |
| 9,723,381 B2 * | 8/2017 | Swanson ................ | G01C 21/20 |
| 9,743,848 B2 * | 8/2017 | Breslow ............ | A61B 5/02405 |
| 10,361,802 B1 * | 7/2019 | Hoffberg-Borghesani ................... G06F 3/00 |  |
| 11,157,572 B1 * | 10/2021 | Anima .............. | G06F 16/24575 |
| 2005/0091184 A1 * | 4/2005 | Seshadri .............. | G06Q 10/107 |
| 2007/0300185 A1 * | 12/2007 | Macbeth ................. | G06F 9/451 715/764 |
| 2010/0197463 A1 * | 8/2010 | Haughay, Jr. ...... | A63B 24/0062 482/8 |
| 2011/0126119 A1 * | 5/2011 | Young ..................... | G06F 3/048 715/744 |

(Continued)

*Primary Examiner* — Sheree N Brown
(74) *Attorney, Agent, or Firm* — JW Law Group; James M. Wu

(57) ABSTRACT

A method and system for influencing or forming a list of activities of a user from the location of the user. In one embodiment, a user is tracked with a GPS mobile tracker. The list of locations the user was present at is correlated with a known locations database to produce a list of user activities, with the type of activity designated by the name of the establishment at the location of the user. A further embodiment cross-references the establishment with a known activities database to filter out spurious records, where the user was not present for long enough or was present for too long for the record to be considered meaningful in an application. A further embodiment uses the location information to deduce information about the health of the user.

18 Claims, 1 Drawing Sheet

(56) References Cited

U.S. PATENT DOCUMENTS

| | | | |
|---|---|---|---|
| 2011/0191697 A1* | 8/2011 | Sumner | H04W 4/02 |
| | | | 715/758 |
| 2011/0276396 A1* | 11/2011 | Rathod | G06Q 20/10 |
| | | | 707/706 |
| 2013/0325394 A1* | 12/2013 | Yuen | A63B 24/0062 |
| | | | 702/150 |
| 2013/0325396 A1* | 12/2013 | Yuen | A61B 5/743 |
| | | | 702/160 |
| 2014/0007010 A1* | 1/2014 | Blom | G06F 3/011 |
| | | | 715/825 |
| 2014/0052790 A1* | 2/2014 | Yuen | A61B 5/14546 |
| | | | 709/204 |
| 2016/0058372 A1* | 3/2016 | Raghuram | A61B 5/681 |
| | | | 600/595 |
| 2016/0328577 A1* | 11/2016 | Howley | G16H 20/60 |
| 2016/0378608 A1* | 12/2016 | Kong | G06F 11/1438 |
| | | | 714/15 |
| 2017/0140041 A1* | 5/2017 | Dotan-Cohen | G06F 16/335 |
| 2017/0259121 A1* | 9/2017 | King | G10L 15/22 |
| 2017/0262164 A1* | 9/2017 | Jain | G06F 9/451 |
| 2017/0357722 A1 | 12/2017 | Rinzler et al. | |
| 2018/0114177 A1* | 4/2018 | Somech | G06Q 10/063118 |
| 2018/0280760 A1* | 10/2018 | Winsper | H04M 1/72412 |
| 2019/0005024 A1* | 1/2019 | Somech | H04L 67/306 |
| 2019/0099124 A1* | 4/2019 | Mattis | A61B 5/0205 |
| 2020/0225908 A1* | 7/2020 | Lee | G06F 3/167 |
| 2022/0148010 A1* | 5/2022 | Partridge | G06Q 30/02 |

\* cited by examiner

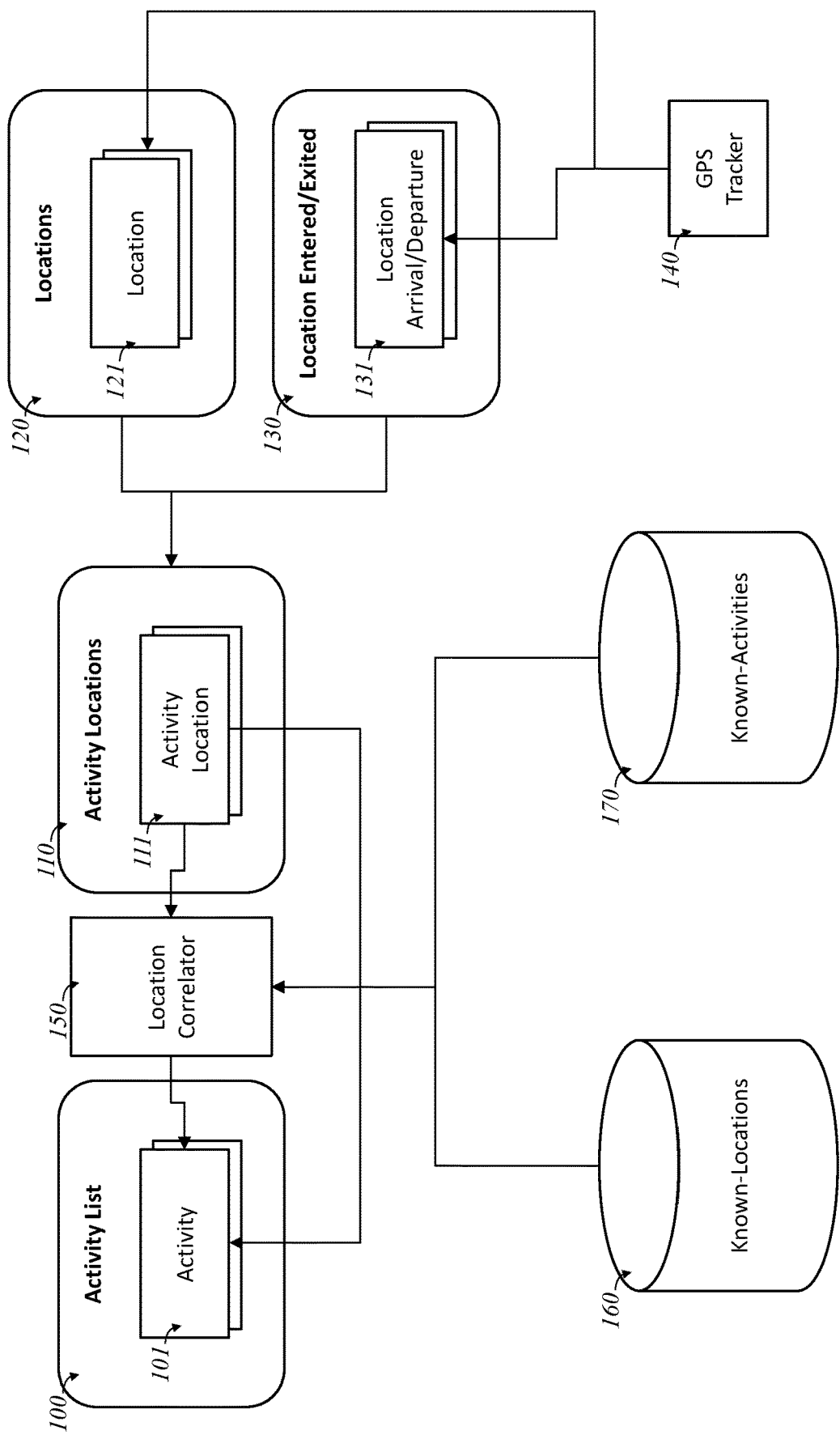

SYSTEM AND METHOD FOR DETERMINING ACTIVITIES OF A USER BASED ON LOCATION

CROSS REFERENCE TO RELATED APPLICATION

This application claims the benefit of provisional patent application Ser. No. 62/543,374, filed Aug. 10, 2017 by the present inventor, the entire content of which is hereby incorporated by reference.

BACKGROUND OF THE INVENTION

1. Field of the Invention

The present invention relates to the field of determining the activities a user has performed or experienced based on the location of the user.

2. Description of the Prior Art

Many applications call for the list of activities the user has performed. In many cases, the users are expected to self-report the data. However, one problem with self-reported data is that the user has to input it, and users can be lazy, forgetful, or even deceitful if they are aware of the purpose of the collection and want to skew the results.

Location tracking is an existing technique known to the art to determine where the user is. A number of different location tracking schemes exist, including using GPS to track the user via a mobile device such as a phone, or using radio beacons to determine the entry or exit of the user into geotagged areas.

People have considered using these locations to automatically generate lists. One such system, disclosed in U.S. patent application Ser. No. 15/589,650, uses the location of the user gathered through GPS to infer a list of interests the user may have. For example, if a user spends a lot of time at record stores, such a system may infer that the user has an interest in music and start targeting advertisements to the user. It's unclear whether this is of benefit to the user himself, or why such a user would opt into or allow such tracking.

However, until now, no one has used these locations to infer the activities that the user has undertaken or participated in himself. And this is a real problem. In the field of health, a list of the activities a user has undertaken could be immensely powerful. Existing fitness applications, such as MyFitnessPal, request users to enter what they have eaten, or how long they have been at the gym. Those applications can go very long stretches of time being neglected by the user, thus reducing the value of the application to the user, sometimes to nothing. If the application could instead infer this information based on the user's location, applications such as these could retain at least some value to the user, and perhaps enough to encourage the user to opt in or allow the application to track the user's location.

The following disclosed invention and its embodiments overcome the problems listed above.

SUMMARY

In accordance with one embodiment, a method and system for determining the activities of a user based in whole or part on location.

BRIEF DESCRIPTION OF THE DRAWINGS

FIG. 1 is a diagram of an embodiment of the invention.

DETAILED DESCRIPTION

FIG. 1 presents the invention. The innovative step is inferring the activity 101 of the user based on the user's location. Determining the location of the user is well known to the art, but using it to infer a list of activities the user underwent is not. The inference may be valuable, as even if the device insistently asks the user to provide some needed data, the user may not remember the accurate data or put garbage data in to dismiss the prompts and return to other activities.

One embodiment of the present invention is to use the user's location as a data source. Another embodiment is to use that data to help guide the collection of activities. Another embodiment uses the data as an input into a machine learning algorithm which produces inferred activities.

One further embodiment uses the inferred activities list to augment an activities list gathered from other sources. Another embodiment uses the inferred activities list to adjust an activities list gathered from other sources. Another embodiment uses the inferred activities list as the activities list directly. A further embodiment uses the name of the establishment the user was at as the identification of the activity.

This may have applications in the field of health as well. For example, a patient may have difficulty inputting high-quality, frequent, data into a meal-logging application about his dietary intake. Or perhaps he eats more than he tells the application. One embodiment assists the process of data collection, and thus may improve data collection, as follows: when the patient enters a place that is known as a restaurant—data available from mapping services—this embodiment records that fact and the time the patient arrived and left. A further embodiment prompts the patient to enter what he ordered. Another embodiment includes the location as well. A further embodiment includes specific questions relating to the overall task or regimen the patient is undergoing, producing output such as "I see you are at McDonalds. Did you eat more than you wanted from your diet? [yes or no]". Another embodiment prompts the user to enter a proper and complete entry of what he ate. Another embodiment records the fact of where and when he entered, and how long he stayed. A further embodiment uses the length of the time at the event, as well as the type of establishment of the event, to determine the health value of the event, in whole or part: one specific embodiment uses standard calorie/hour consumption rates at restaurants and eating establishments, by multiplying that consumption rate by the time spent; another uses standard calorie/hour burn rates at gyms and fitness events by multiplying that rate by the time spent. The availability of such rates in the aggregate is widely disseminated, and the construction of subaggregates is known to the art. One embodiment takes into account the patient's and/or doctor's desire for rigor in compliance to determine what the prompts are and how aggressive they are. Another embodiment takes into account the quality of the data or the confidence the invention has in the analytic conclusions—for example, if the meal log is needed to help predict the specific disorder of diabetes, and yet there are obvious holes in the log, one embodiment allows tuning to automatically increase the level of prompting and insistence to drive better compliance without the patient or practitioner needing to ask for more insistence. Another embodiment collects available locations, based on a local, patient-provided, doctor-provided, population-specific, or general filter. These locations need not be food related: visiting a gym for more than a moment may provide a window into possible exercise, visiting a resort may provide a window into possible relaxation, etc. One embodiment creates gym activity records based on the user's time spent at a gym via the location records. Another embodiment generates inferred food consumption records based on the user's time spent at a restaurant. A further embodiment log the locations, with or without time, place, or other attendant or recorded behaviors, etc. Another embodiment increases counters. Another embodiment correlates the location with other abstract or summary results, and provides those derived results, which May be used by any part of the system. One embodiment uses these results to produce short- or long-running (even lifetime) deductions and predictions.

How to track the location of a user is known to the art. One embodiment of such is now presented. The user possesses a mobile device with a GPS tracking system 140. As the user moves, the GPS tracking system 140, at intervals either regularly determined, based on significant movement, or both, provides an update of the location 121 of the user, producing a list of locations 120. In one further embodiment, if the user should pause for a length of time, the system generates a location arrival record 131 corresponding to the arrival of the user at a location. In another further embodiment, when the user leaves such a location after such an arrival message has been generated, the system generates a location departure record 131. A further embodiment generates both arrival and departure records. (Both share the same number because their format is identical, with a one-bit column designating the entry as arrival or departure in one embodiment.) These records are compiled into a list 130.

The records of 120 or 130 or both are cross referenced with a known-locations database 160, such as the one present in Google Maps. In one embodiment, the arrival records 131 are cross-referenced with said known-locations database 160, producing a list 110 of inferred activity locations 111 with the amount of time spent at each location derived from the exited time of the location exited record minus the entered time of the location entered record for the same location and time period. In another embodiment, the location records themselves are cross-referenced with the known-locations database, producing a list of inferred activity locations with inferred activity times. One further embodiment produces the inferred activity times by taking the midpoint of the time of a location record and the following record, and subtracting from that the midpoint of the time of the same location record and the previous record.

In one embodiment, these activity location records are declared the list 100 of inferred activity records 101, with the location being the activity tag. In another embodiment, these activity location records are further cross-referenced with the type-of-location tag of the known-locations database to derive the type of activity, which is then given as the activity tag. In another embodiment, the activity list is further filtered by the time the user was spent at the location, correlated through a known-activities database 170 that specifies elements of the statistical distribution of time to the activity. The goal is to filter out activity records that are too short in time, too long in time, or otherwise incompatible with the activity.

In one embodiment, the known-activities database is refined by the name or identifier of the establishment present at the location: for example, McDonald's is a part of the primary key of the database in this embodiment. In another embodiment, the known-activities database is refined by the type of the establishment present at the location: for example, McDonald's is a fast food restaurant, and a label representing "fast food" is a part of the primary key of the database in this embodiment. In one embodiment, the statistical distribution record in the database comprises a minimum time (may be null for events with no minimum time) and maximum time (may be null for events with no maximum time).

Activity records whose time falls outside of the statistical distribution record of the known-activities database are filtered out in one embodiment. In another, they are given lower weight: a specific embodiment is to assign the weight to be 1 if the activity falls within the range, $t/Tmin$ where $t$ is the duration of the activity and $Tmin$ is the minimum activity duration if the duration $t$ is less than the activity time $Tmin$, or $Tmax/t$ where $t$ is the duration of the activity and $Tmax$ is the maximum activity duration. Another embodiment clips the time of the activity to the maximum activity duration. Another embodiment clips the time of the activity to a statistical result of the activity according to the user: for example, one embodiment limits the excessive record to the average time the user spent performing such activities. The value of this may be to eliminate or reduce the importance of records that do not make as much sense relative to the activity: if a user spent only five minutes at a restaurant, it is unlikely that the user consumed significant calories there at that moment. If a user spent a day at a gym, it is unlikely that the user exercised for a day, but rather probably forgot her phone after working a typical workout.

In the description herein, one or more embodiments of the invention are described, with process steps and functional interactions. Those skilled in the art would realize, after perusal of this application, that embodiments of the invention might be implemented using a variety of other techniques not specifically described, without undue experimentation or further invention, and that such other techniques would be within the scope and spirit of the invention. The use of the words "can" or "may" in regards to the structure and operation of embodiments is to be construed as referring to further embodiments and configuration options, and does not require further experimentation or invention.

The scope and spirit of the invention is not limited to specific examples disclosed therein, but is intended to include the most general concepts embodied by these and other terms.

Although the invention has been described with reference to several exemplary embodiments, it is understood that such descriptions and illustrations are not limiting. Changes May be made within the purview of the appended claims, as presently stated, without departing from the scope and spirit of the invention in its aspects. Although the invention has been described with reference to particular means, materials, machines, and embodiments, the invention is not intended to be limited to the particulars disclosed; rather, the invention extends to all functionally equivalent structures, methods, machines, and uses such as are within the scope of the invention and claims.

I claim:

1. A method for operating a mobile device to infer activity of a user comprising steps of:

maintaining on the mobile device, a database of known locations, wherein each location is associated with one or more activities performed by the user and entered into the database by the user;

identifying locations visited by the mobile device and a visit time duration associated with each location that is visited;

determining that for a selected location, the user failed to enter an activity performed by the user at the selected location;

comparing a selected visit time duration for the selected location to a range of durations, wherein when the selected visit time duration is within the range of durations, the the activity of the user that the user failed to enter is inferable;

determining, when the activity of the user is inferable, inferred activity of the user for the activity of the user that the user failed to enter based on the selected visit time duration; and entering into the database, the inferred activity of the user for the activity of the user that the user failed to enter.

2. The method of claim 1, wherein said inferred activity of the user is related to health of the user.

3. The method of claim 1, further comprising performing an action that prompts the user to confirm that the inferred activity of the user is what the user performed.

4. The method of claim 3, wherein the action leads to at least one of augment and replace one or more of the inferred activity of the user.

5. The method of claim 3, comprising further steps of:
providing standard rates of measurement changes expected for at least one known activity, and correlating a candidate known activity with standard rates to produce said inferred activity of the user.

6. The method of claim 5, wherein the user was at a known location for fitness and the inferred activity of the user is inferred calories expended.

7. The method of claim 5, wherein the user was at a known location for eating and the inferred activity of the user is inferred calories consumed.

8. A system for inferring activity of a user, the system comprising:
a mobile device having a global positioning system (GPS) and configured to perform operations of:
maintaining on the mobile device, a database of known locations, wherein each location is associated with one or more activities performed by the user and entered into the database by the user;
identifying locations visited by the mobile device and a visit time duration associated with each location that is visited;
determining that for a selected location, the user failed to enter an activity performed by the user at the selected location;
comparing a selected visit time duration for the selected location to a range of durations, wherein when the selected visit time duration is within the range of durations, the activity of the user that the user failed to enter is inferable;
determining, when the activity of the user is inferable, inferred activity of the user for the activity of the user that the user failed to enter based on the selected visit time duration; and
entering into the database, the inferred activity of the user for the activity of the user that the user failed to enter.

9. The system of claim 8, wherein said inferred activity of the user is related to the health of the user.

10. The system of claim 8, further comprising performing an action that prompts the user to confirm that the inferred activity of the user is what the user performed.

11. The system of claim 10, wherein the action leads to at least one of augment and replace one or more of the activities of the user.

12. The system of claim 10, the operations further comprising: providing standard rates of measurement changes expected for at least one known activity, and correlating said candidate known activity with said standard rates to produce said inferred activity of the user data.

13. The system of claim 12, wherein the user was at a known location for fitness and the inferred activity of the user determined from the known location is inferred calories expended.

14. The system of claim 12, wherein the user was at a known location for eating and the inferred activity of the user is inferred calories consumed.

15. The method of claim 1, comprising a further step of: filtering said missing activity of the user based on at least one of a minimum, and a maximum expected duration for said missing activity of the user.

16. The method of claim 15, wherein said filtering is performed by assigning a weight to said activity of the user based on the degree to which said missing activity of the user falls within a range of minimum and maximum expected durations.

17. The system of claim 8, wherein the device is configured to perform filtering by assigning a weight to said missing activity of the user based on the degree to which said missing activity of the user falls within a range of minimum and maximum expected durations.

18. The system of claim 17, wherein said filtering is performed by assigning a weight to said missing activity of the user based on the degree to which said missing activity of the user falls within a range of minimum and maximum expected durations.

* * * * *